(12) United States Patent
Freed

(10) Patent No.: US 8,583,240 B2
(45) Date of Patent: Nov. 12, 2013

(54) DEVICE AND METHOD FOR TREATING DYSPHAGIA WITH ELECTRICAL STIMULATION

(76) Inventor: Marcy L. Freed, Tulalip, WA (US)

( * ) Notice: Subject to any disclaimer, the term of this patent is extended or adjusted under 35 U.S.C. 154(b) by 0 days.

(21) Appl. No.: 13/443,372

(22) Filed: Apr. 10, 2012

(65) Prior Publication Data

US 2013/0023952 A1 Jan. 24, 2013

Related U.S. Application Data

(60) Provisional application No. 61/509,504, filed on Jul. 19, 2011.

(51) Int. Cl.
*A61N 1/18* (2006.01)
(52) U.S. Cl.
USPC .............................. 607/48; 607/72
(58) Field of Classification Search
USPC ...................................... 607/48, 72
See application file for complete search history.

(56) References Cited

U.S. PATENT DOCUMENTS

| | | | |
|---|---|---|---|
| 3,277,892 A | 10/1966 | Tepper | |
| 3,480,010 A | 11/1969 | Crossley | |
| 3,805,769 A | 4/1974 | Sessions | |
| 3,881,495 A | 5/1975 | Pannozzo | |
| 3,911,906 A | 10/1975 | Reinhold, Jr. | |
| 3,946,745 A | 3/1976 | Hsiang-Lai | |
| 3,989,051 A | 11/1976 | Nozhnikov | |
| 3,993,049 A | 11/1976 | Kater | |
| 4,066,078 A | 1/1978 | Berg | |
| 4,140,133 A | 2/1979 | Kastrubin | |
| 4,167,190 A | 9/1979 | Sorenson | |
| 4,244,373 A | 1/1981 | Nachman | |
| 4,254,776 A | 3/1981 | Tanie | |
| 4,390,023 A | 6/1983 | Rise | |
| 4,411,268 A | 10/1983 | Cox | |
| 4,489,440 A | 12/1984 | Chaoui | |
| 4,505,275 A | 3/1985 | Chen | |
| RE31,866 E | 4/1985 | Lines | |
| 4,509,521 A | 4/1985 | Barry | |
| 4,519,400 A | 5/1985 | Brenman | |
| 4,527,037 A | 7/1985 | Johnson | |
| 4,537,195 A | 8/1985 | McDonell | |
| 4,580,570 A | 4/1986 | Sarrell | |
| 4,688,574 A | 8/1987 | Dufresne | |
| 4,690,145 A | 9/1987 | King-smith | |
| 4,706,680 A | 11/1987 | Keusch | |
| 4,715,367 A | 12/1987 | Crossley | |
| 4,759,368 A | 7/1988 | Spanton | |
| 4,763,656 A | 8/1988 | Nauman | |

(Continued)

*Primary Examiner* — Joseph Dietrich
(74) *Attorney, Agent, or Firm* — Dean A. Craine

(57) ABSTRACT

An electrical stimulation device and non-invasive method for treating dysphagia and artificially promoting swallowing by simultaneous electrical stimulation of the pharyngeal and facial muscles. The device includes a plurality of electrodes selectively placed in electrical contact with pharyngeal and oral-facial regions of a patient and a series of electrical pulses in electrical contact with each of the plurality of electrodes with a generator. The generator includes a pulse rate modulator for generating electrical pulses having a frequency generally fixed at 80 hertz, a pulse width modulator for generating a series of electrical pulses each at a duration fixed at 300 microseconds, and a governor for regulating the electrical pulses such that at least one of current does not to exceed 4.4 milliamps RMS or power does not to exceed 9.6 MW RMS. The electrical pulses selectively stimulate muscles located proximate to the electrodes to close the mouth and initiate swallowing.

6 Claims, 9 Drawing Sheets

(56) References Cited

U.S. PATENT DOCUMENTS

| | | | |
|---|---|---|---|
| 4,777,954 A | 10/1988 | Keusch | |
| 4,786,277 A | 11/1988 | Powers | |
| 4,793,353 A | 12/1988 | Borkan | |
| 4,813,418 A | 3/1989 | Harris | |
| 4,827,935 A | 5/1989 | Geddes | |
| 4,830,008 A | 5/1989 | Meer | |
| 4,860,754 A | 8/1989 | Sharik | |
| 4,867,164 A | 9/1989 | Zabara | |
| 4,895,154 A | 1/1990 | Bartlet | |
| 4,907,602 A | 3/1990 | Sanders | |
| 4,919,139 A | 4/1990 | Brodard | |
| 4,926,865 A | 5/1990 | Oman | |
| 4,926,878 A | 5/1990 | Snedeker | |
| 4,989,607 A | 2/1991 | Keusch | |
| 5,016,647 A | 5/1991 | Sanders | |
| 5,025,807 A | 6/1991 | Zabara | |
| 5,033,469 A | 7/1991 | Brodard | |
| 5,107,835 A | 4/1992 | Thomas | |
| 5,109,847 A | 5/1992 | Liss | |
| 5,111,814 A | 5/1992 | Goldfarb | |
| 5,133,354 A | 7/1992 | Kallok | |
| 5,146,918 A | 9/1992 | Kallok et al. | |
| 5,178,156 A | 1/1993 | Takishmia | |
| 5,183,041 A | 2/1993 | Toriu | |
| 5,269,303 A | 12/1993 | Wernicke | |
| 5,285,781 A | 2/1994 | Brodard | |
| 5,299,569 A | 4/1994 | Wernicke | |
| 5,397,338 A | 3/1995 | Grey | |
| 5,406,945 A | 4/1995 | Riazzi | |
| 5,423,869 A | 6/1995 | Poore | |
| 5,427,096 A | 6/1995 | Bogusiewicz | |
| 5,511,548 A | 4/1996 | Riazzi | |
| 5,540,033 A | 7/1996 | Fox | |
| 5,540,734 A | 7/1996 | Zabara | |
| 5,540,736 A | 7/1996 | Haimovich | |
| 5,571,150 A | 11/1996 | Wernicke | |
| 5,578,061 A | 11/1996 | Stroetmann | |
| 5,658,318 A | 8/1997 | Stroetmann | |
| 5,678,535 A | 10/1997 | DiMarco | |
| 5,707,400 A | 1/1998 | Terry | |
| 5,725,564 A * | 3/1998 | Freed et al. | 607/72 |
| 5,755,745 A | 5/1998 | McGraw | |
| 5,848,966 A | 12/1998 | Gusakov | |
| 5,851,223 A | 12/1998 | Liss | |
| 5,891,185 A * | 4/1999 | Freed et al. | 607/72 |
| 5,911,218 A | 6/1999 | DiMarco | |
| 5,921,925 A | 7/1999 | Cartmell | |
| 5,987,359 A | 11/1999 | Freed | |
| 6,023,631 A | 2/2000 | Cartmell | |
| 6,064,901 A | 5/2000 | Cartmell | |
| 6,076,002 A | 6/2000 | Cartmell | |
| 6,104,958 A | 8/2000 | Freed | |
| 6,129,666 A | 10/2000 | DeLuca | |
| 6,134,480 A | 10/2000 | Minogue | |
| 6,141,575 A | 10/2000 | Price | |
| 6,480,731 B1 | 11/2002 | DeLuca | |
| 6,587,725 B1 | 7/2003 | Durand et al. | |
| 6,587,727 B2 | 7/2003 | Osorio et al. | |
| 6,745,082 B2 | 6/2004 | Axelgaard | |
| 6,770,022 B2 | 8/2004 | Mechlenburg | |
| 6,770,725 B2 | 8/2004 | Santerre | |
| 6,915,148 B2 | 7/2005 | Finneran | |
| 7,082,331 B1 | 7/2006 | Park | |
| 7,177,691 B2 | 2/2007 | Meadows | |
| 7,245,957 B2 | 7/2007 | Rowe | |
| 7,245,971 B2 | 7/2007 | Park | |
| 7,277,749 B2 | 10/2007 | Gordon et al. | |
| 7,280,873 B2 | 10/2007 | Freed | |
| 8,160,712 B1 | 4/2012 | Freed | |
| 2001/0010010 A1 | 7/2001 | Richmond et al. | |
| 2003/0153954 A1 | 8/2003 | Park et al. | |
| 2003/0195571 A1 | 10/2003 | Burnes et al. | |
| 2003/0216789 A1 | 11/2003 | Deem et al. | |
| 2006/0224211 A1 | 10/2006 | Durand et al. | |
| 2006/0276701 A1 | 12/2006 | Ray | |
| 2007/0156182 A1* | 7/2007 | Castel et al. | 607/2 |
| 2008/0021506 A1 | 1/2008 | Grocela | |
| 2008/0109047 A1 | 5/2008 | Pless | |

* cited by examiner

DEVICE AND METHOD FOR TREATING DYSPHAGIA WITH ELECTRICAL STIMULATION

This utility patent application is based on and claims the filing date benefit of U.S. provisional patent application (Application No. 61/509,504) filed on Jul. 1, 2011.

Notice is hereby given that the following patent document contains original material which is subject to copyright protection. The copyright owner has no objection to the facsimile or digital download reproduction of all or part of the patent document, but otherwise reserves all copyrights whatsoever.

BACKGROUND OF THE INVENTION

1. Field of the Invention

This invention relates to a device and method for effectively treating dysphagia. In particular, the present invention relates to a device and method for treating dysphagia by providing simultaneous electrical stimulation to the facial and pharyngeal regions on an afflicted person.

2. Description of the Related Art

Dysphagia is the inability of difficulty in swallowing and may be caused by stroke, neurodegenerative diseases, or a respiratory disorder. Swallowing is a complicated action which is usually initiated voluntarily but always completed reflexively, whereby food is moved from the mouth through the pharynx and esophagus to the stomach. The act of swallowing occurs in three stages and requires the integrated action of the respiratory center and motor functions of multiple cranial nerves, and the coordination of the autonomic system within the esophagus.

In the first stage, food is placed on the surface of the tongue. The tip of the tongue is placed against the hard palate. Elevation of the larynx and backward movement of the tongue forces the food through the isthmus of the fauces in the pharynx. In the second stage, the food passes through the pharynx. This involves constriction of the walls of the pharynx, backward bending of the epiglottis, and an upward and forward movement of the larynx and trachea. Food is kept from entering the nasal cavity by elevation of the soft palate and from entering the larynx by closure of the glottis and backward inclination of the epiglottis. During this stage, respiratory movements are inhibited by reflex. In the third stage, food moves down the esophagus and into the stomach. This, movement is accomplished by momentum from the second stage, peristaltic contractions, and gravity. Although the main function of swallowing is the propulsion of food from the mouth into the stomach, swallowing also serves as a protective reflex for the upper respiratory tract by removing particles trapped in the nasopharynx and oropharynx, returning materials refluxed from the stomach into the pharynx, or removing particles propelled from the upper respiratory tract into the pharynx. Therefore, the absence of adequate swallowing reflex greatly increases the chance of pulmonary aspiration.

In the past, exclusive electrical stimulation of the throat to treat dysphagia has been used and is disclosed by the inventor in U.S. Pat. Nos. 6,104,958 and 5,987,359, and now incorporated by reference herein. While is it known that a person is unable to swallow while his or her mouth is open, what is needed is a device that simultaneously electrically stimulates both the facial and pharyngeal regions of the head to promote swallowing.

SUMMARY OF THE INVENTION

The above stated needs are met by the device and method for providing a simple, non-invasive device and method for treating dysphagia by simultaneous stimulating the pharyngeal and facial regions of the head. The device includes an electrical stimulator that generates electrical pulses of a selected amperage and duration to eight electrodes attached to selected muscles located in the pharyngeal and facial regions. Four electrodes are attached to the anterior pharyngeal region of the throat and used to stimulate pharyngeal muscles that stimulate nerves that control swallowing. Four electrodes are attached to opposite sides of the face which stimulate facial nerves that cause contraction or closure of the mouth. By simultaneously stimulating both the pharyngeal and facial muscles, patients are able to swallow sooner (less treatments sessions required to see a self-generated swallowing) and more completely and effectively stimulate muscles around the mouth and tongue. The stimulator includes a pulse rate modulator for generating eight electrical pulses each having a frequency generally fixed at 80 hertz, a pulse width modulator for generating each pulse of the series of electrical pulses at a duration generally fixed at 300 microseconds, and a governor for regulating the electrical pulses such that at least one of the current so as not to exceed 4.4 milliamps RMS or power so as not to exceed 9.6 MW RMS.

DESCRIPTION OF THE PREFERRED EMBODIMENT(S)

Figure 1:
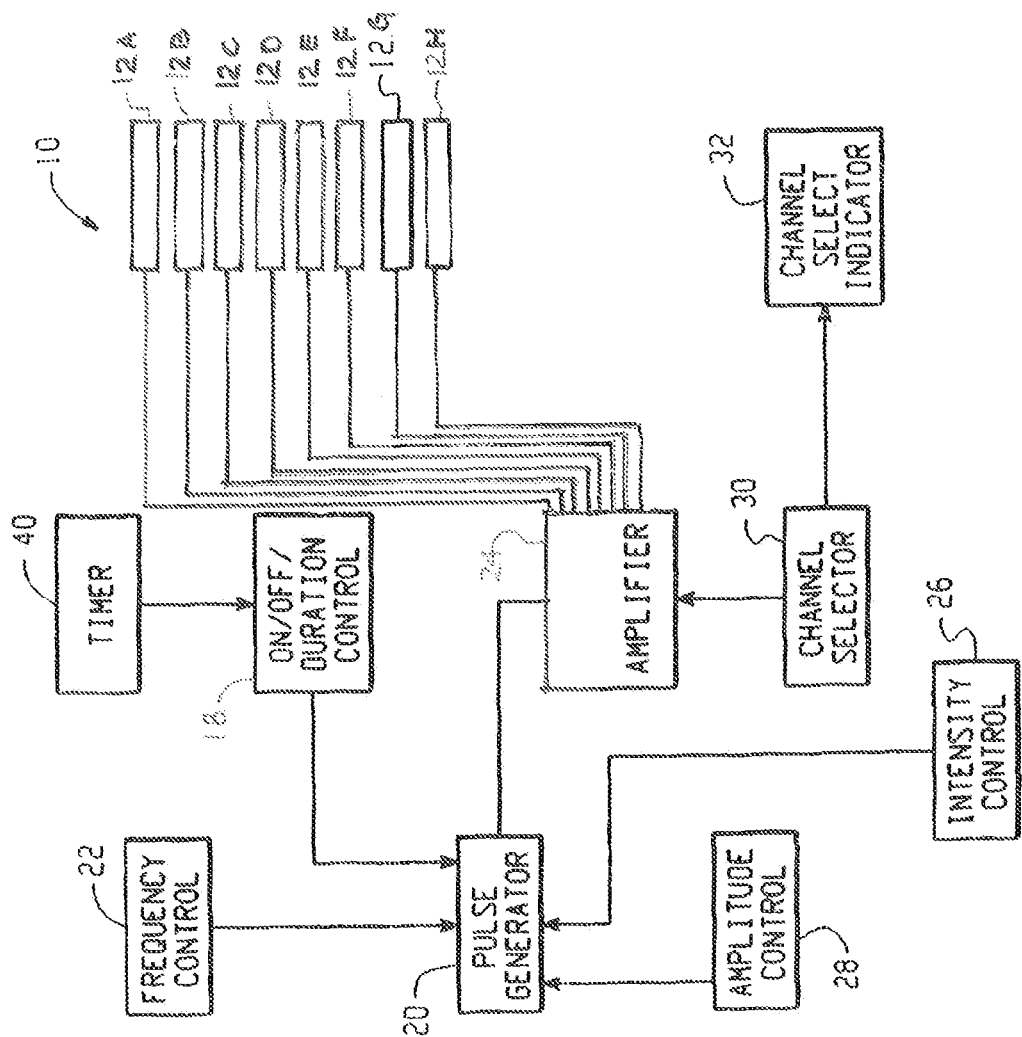
FIG. 1 is a simplified fragmentary illustration of an electrical pharyngeal neuromuscular stimulator for use in promoting swallowing according to the present invention.

This invention is directed to a simple, non-invasive method and device for electrical facial and pharyngeal neuromuscular stimulation for artificially promoting swallowing wherein electrical stimulus is provided to facial region to close the mouth and sequentially to the pharyngeal region of a patient to stimulate muscles located in the pharyngeal region in order to promote swallowing. Referring now to the drawings wherein the showings are for the purposes of illustrating the preferred embodiment of the invention only and not for purposes of limiting same, the electrical pharyngeal neuromuscular stimulation device 10 as shown in FIG. 1 is comprised of a eight electrodes 12a-h adapted to be selectively placed in electrical contact with tissue of a pharyngeal region of a patient and a generator 20 for generating a series of electrical pulses in electrical contact with each of the plurality of electrodes.

The device 10 is preferably comprised of eight electrodes 12a-h. Each electrode is preferably made of metal or some other physiologically acceptable conductive material. In general, the electrodes 12a-h are suitably any conventional and convenient shape which is suited for physiological applications and include an anode contact and a cathode contact. Lead wires 14 are attached to each electrode and are suitable for attachment to the generator 20. The lead wires 14 are made from any physiologically acceptable conductive metal, preferably insulated aluminum wire.

The device 10 electrical simulator 30 that includes an outer housing 32 with a PCB 34 and a battery pack (not shown) mounted therein. Formed on the PCB 34 are eight electrical stimulating channels 36a-h that are connected in a parallel manner to simultaneously provide an electrical pulse 100 to connect each channel port 11a-h, respectively. Mounted on the outer housing 32 and electrically connected to the PCB 34 is a main power switch 42, a main power timer switch 43, eight pairs of voltage or amplitude control switches 44a-h, 46a-h, eight channel electrode wire ports 11a-h, an LCD display 80, an adjustable delay timer switch 85, and an amplitude lock switch 90.

The device 10 is very similar to the neuromuscular electrical stimulator (known as a NMES) used in the treatment of dysphagia sold by Chattanooga Group of Hixson, Tenn. under the trademark VITALSTIM.

The subject wave forms are suitably realized by selective control of a pulse generator 20 working in connection with an amplifier 18. The generator 20 is comprised of a pulse rate modulator or a frequency controller 22 for generating each of the electrical pulses having a frequency generally fixed at 80 hertz. The generator 20 is also comprised of a pulse width modulator suitably accomplished by an on/off/duration control 24 for generating each pulse of the series of electrical pulses at a duration generally fixed at 300 microseconds. The generator 20 is further comprised of a governor 26 for regulating the electrical pulses such that the electrical current does not exceed 4.4 milliamps RMS, the power does not exceed 9.6 MW RMS, or both. The current applied will vary depending on the physical condition and tolerance of the patient but the current applied should be sufficient to produce the desired response and promote the swallowing reflex. The intensity of the current is increased by small increments until the tolerance and comfort level limits are reached in the patient. However, the current which is applied must not be too intense and therefore, result in laryngeal spasms or cardiac arrhythmia in the patient. Another input to pulse generator 20 is formed from amplitude control module 28. The amplitude control module 28 allows for selective control of an amplitude of pulses generated from pulse generator 20. The channel selector 30 suitably forms another input to amplifier 18 to allow for concurrent activation of sets of electrodes 12. The status of channel selector 30 is advantageously indicated by channel selector indicator 32.

In one embodiment of the present invention, the generator 20 continuously generates electrical pulses for a predetermined period of time. Preferably, electric pulses are continuously generated and delivered to the electrodes until a complete swallow is achieved or the tolerance level is reached in the patient. Additional treatments wherein the generator continuously generates electric pulses are suitably performed on the patient as necessary.

In another embodiment of the present invention, the generator 20 selectively generates cycles of electrical pulses. The generator 20 is further comprised of a treatment time controller which is also suitably accomplished with the control 26 real time information which is provided by a timer 40. The timer 40, control 26, and pulse generator 16 also serve to provide functions of a treatment off-time controller, an on-ramp controller, and an off-ramp controller Treatment time control selectively controls the duration of time wherein the generator selectively generates cycles of electric pulses. The treatment time is any suitable period, such as fifteen, thirty, or sixty minutes. As with all settings, the particular values are highly application and patient specific. Thus, a suitable duration of the electric pulses in each cycle is set. Preferably, the duration of electric pulses in each cycle is the range of about 0.5 seconds to about 30 seconds. A selection is made for an amount of time between each cycle. Preferably, the amount of time between cycles is from about 0.1 seconds to about 60 seconds. A selection is also made for the amount of time required to reach the maximum intensity in each cycle. Preferably, the amount of time required to reach the maximum intensity is between about 0.1 seconds to about 6.0 seconds. A selection is further made for the amount of time required to decrease from the maximum intensity to zero intensity at the end of each cycle. Preferably, the amount of time required to decrease from the maximum intensity to zero intensity is between about 0.1 seconds to about 6.0 seconds. A suitable commercially available device which provides the functions described above is found in Staodyn®. EMS+2 System manufactured by Staodyn, Inc. and described in the associated instruction manual which is herein incorporated by reference.

Figure 2:
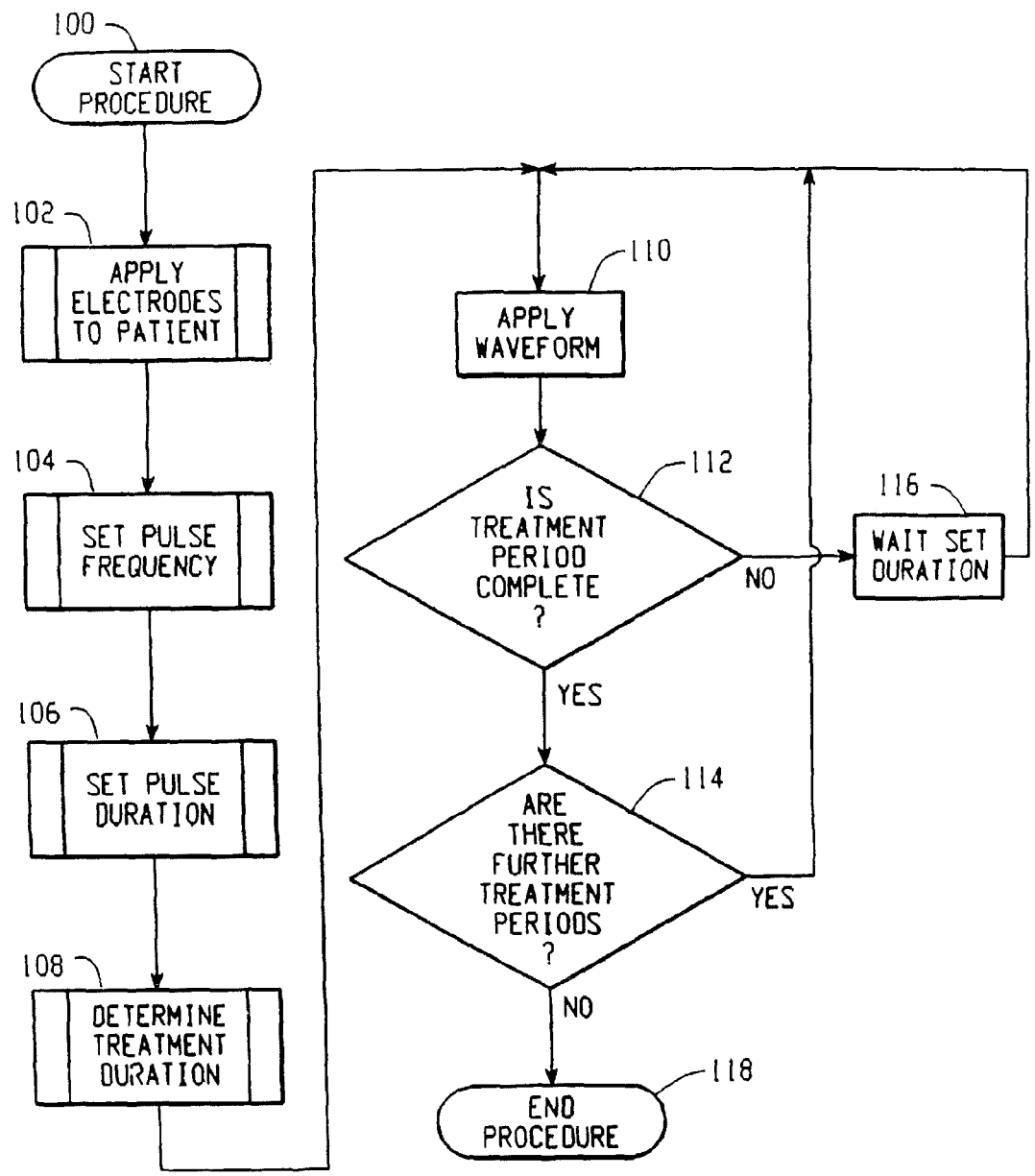
FIG. 2 is a flow chart of a method for electrical pharyngeal neuromuscular stimulation for promoting swallowing according to the present invention.
Figure 3:
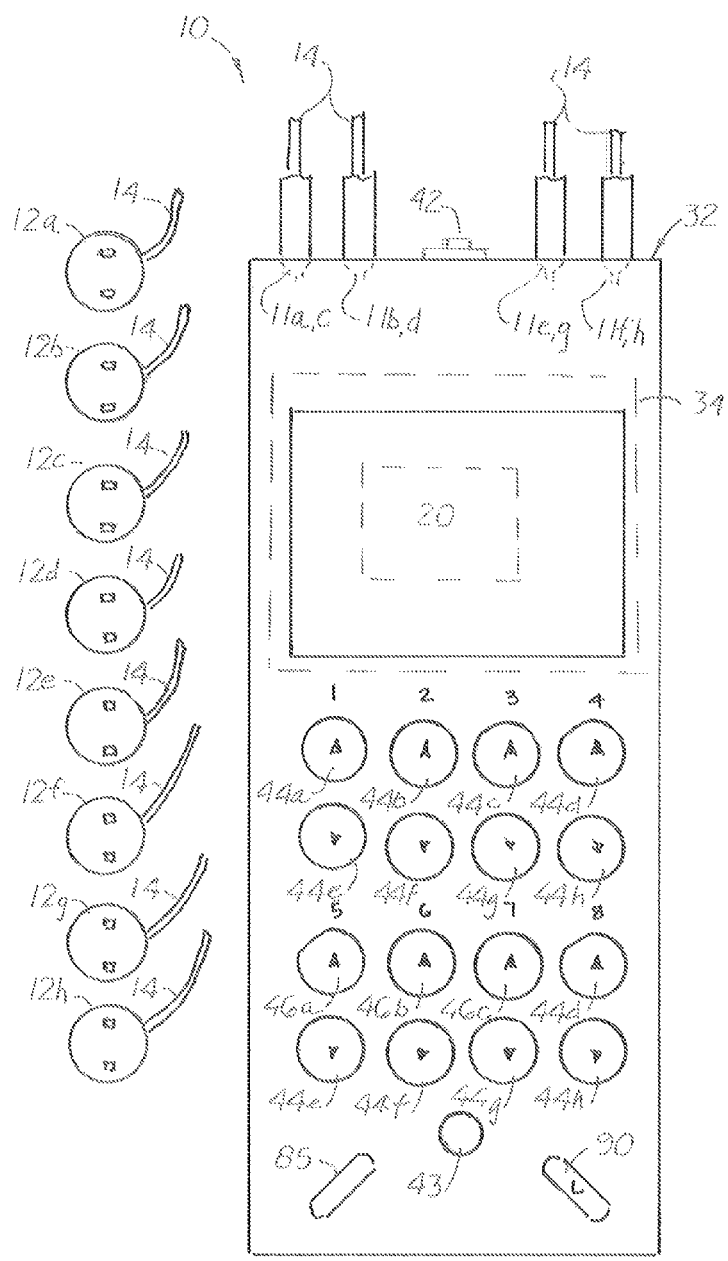
FIG. 3 is a front plan view of the eight electrode electrical stimulator control unit
Figure 4:
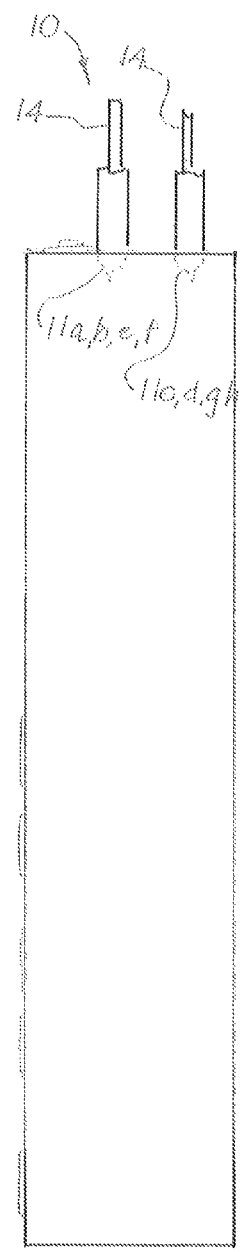
FIG. 4 is a side elevational view of the eight electrode electrical stimulator control unit shown in FIG. 3.

FIG. 2 provides a flow chart of the method for electrical pharyngeal neuromuscular stimulation for promoting swallowing according to the present invention. Turning to block 100, the procedure for treating dysphagia with electrical stimulation is commenced. Next, at block 102, actual electrodes are applied to the pharyngeal area of a patient. The particulars for electrode placement and selection have been disclosed elsewhere in the subject application.

Turning next to block 104, a pulse frequency is set in accordance with the parameters disclosed above. Similarly, at block 102, pulse duration is set. Finally, at block 108, a determination of a treatment duration is made, as well as to the number of treatment periods which are to be applied.

Turning next to block 110, an actual waveform associated with the previously selected parameters is applied to the pharyngeal area of a patient. Next, at block 112, a determination is made as to whether a treatment period has been completed in accordance with the preselected standards. A positive determination causes progress to decision block 114 and a negative determination causes progress to block 116. At block 116, a set duration is applied as a wait period for which progress is returned to block 110, as described above.

At block 114, a determination is made as to whether there are further treatment periods merited. A positive determination causes a return to block 110, Negative determination signals completion of the treatment procedure and progress to termination block 118.

Two facial electrodes 12a, 12b are selectively placed alone a line that extends medially from the ear canal to the corner of the mouth. Two additional facial electrodes 12c, 12d are placed on a line that extends medially from the ear canal to the adjacent corner of the mouth. The electrodes on the same side of the face, 12a, 12b and 12c, 12d are 1 to 1½ inch apart as shown in FIG. 6-9 and as partially shown in FIG. 10.

Depending on the size of the patent, either two or four pharyngeal electrodes 12(e-h) may be used. The pharyngeal electrodes 12 e-h are typically arranged in one of four possible configurations as shown in FIGS. 6-9. The placement of the electrodes in the pharyngeal region of the patient is based on several factors, such as the extent and type of dysphagia exhibited by the patient and, given the extent and type of dysphagia exhibited, those locations within the pharyngeal region, when subjected to electrical stimulus, have the possibility of eliciting the strongest and most complete swallow. An evaluation for swallowing ability is done on the patient to determine the extent and type of dysphagia. The critical elements in the evaluation are to determine the presence of a gag reflex, a dry swallow, and ability to tolerate one's own secretions. The placement of the electrodes 12(e-h) may be changed several times in an effort to obtain the strongest and most effective treatment.

Figure 6:
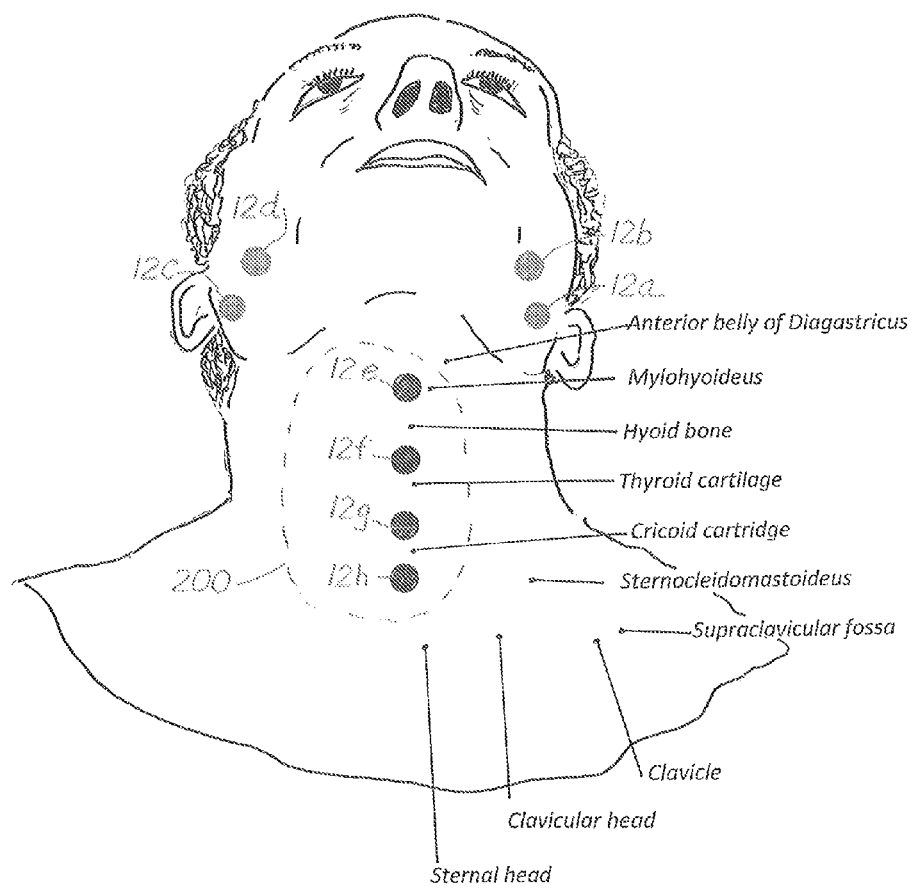
FIG. 6 is a front view of a patient showing the placement of four electrodes longitudinally aligned on the skin of the pharyngeal region starting at the mylohyodeus and terminating just below the Cricoid cartridge and two pairs of facial electrodes on opposite sides of the face

In the first configuration, shown FIG. 6, four electrodes 202 are longitudinally aligned on the skin of the pharyngeal region 200 starting at the mylohyodeus and terminating just below the Cricoid cartridge.

Figure 7:
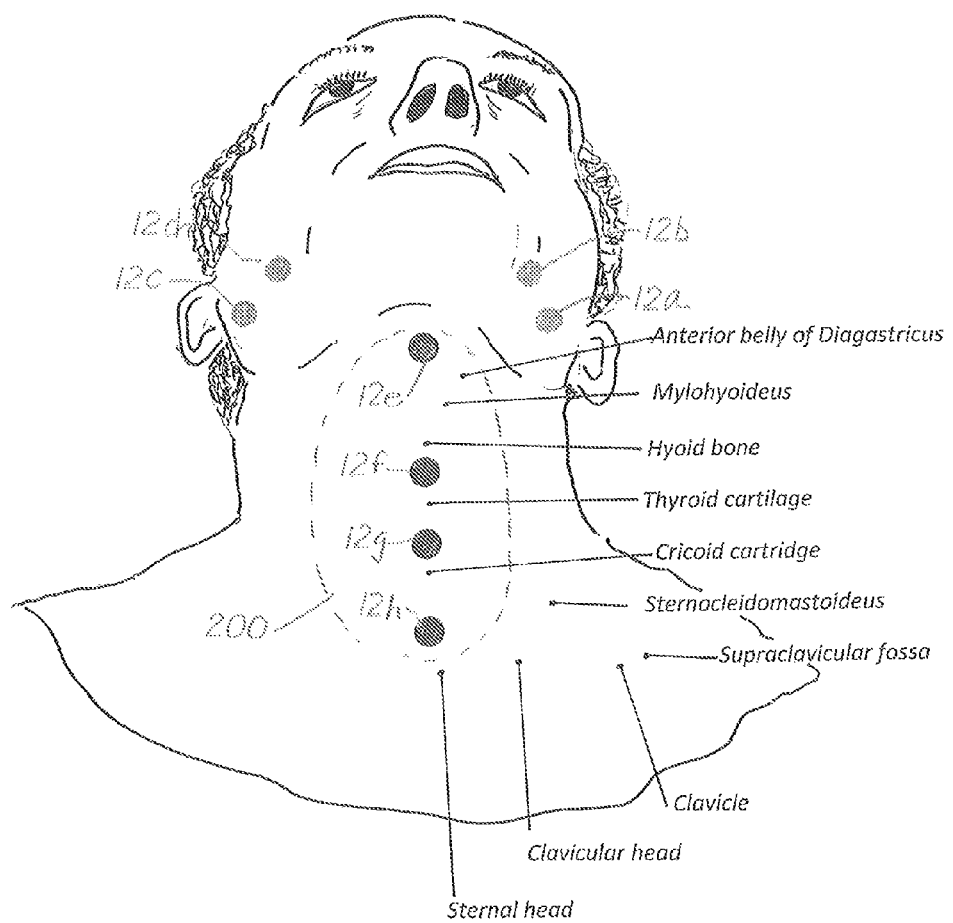
FIG. 7 is a front view of a patient showing the placement of the four electrodes longitudinally aligned on the skin of the pharyngeal region starting at the anterior belly of Diagatricus, the second electrode being located just below the hyoid bone, the third electrode being located just below the thyroid cartridge, and the fourth electrode being located below the cricoid cartridge, and the two pairs of facial electrodes on opposite sides of the face.

In the second configuration, shown in FIG. 7, second embodiment of the present invention, shown in FIG. 7, four electrodes 208 are longitudinally aligned on the skin of the pharyngeal region 200 starting at the anterior belly of Diagatricus. The second electrode 12f is located just below the hyoid bone, the third electrode being located just below the thyroid cartridge, and the fourth electrodes 12h being located below the cricoid cartridge.

Figure 8:
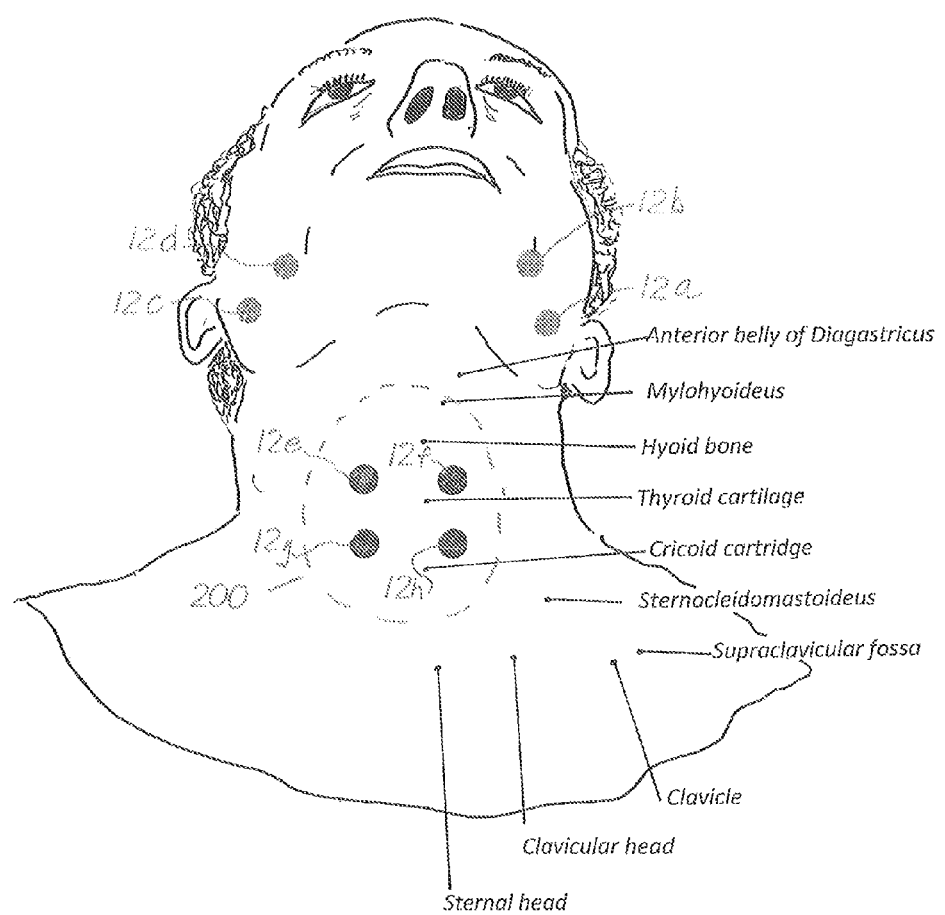
FIG. 8 is a front view of a patient showing the placement of four electrodes positioned on the skin of the pharyngeal region with two pairs of electrodes being positioned on opposite sides of the longitudinal axis with the top two electrodes being positioned in the space between the hyoid bone and the thyroid cartridge, the bottom two electrodes being positioned in the space located between the thyroid cartridge and the cricoids cartridge, and the two pairs of facial electrodes on opposite sides of the face.

In a third configuration, shown in FIG. 8, the four electrodes 12e-12h are positioned on the skin of the pharyngeal region 200 with two pairs of electrodes 12e, 12g and 12f, 12h being positioned on opposite sides of the longitudinal axis. The top two electrodes 12e, 12f are positioned in the space between the hyoid bone and the thyroid cartridge. The bottom two electrodes 12g, 12h, are positioned in the space located between the thyroid cartridge and the cricoids cartridge.

Figure 9:
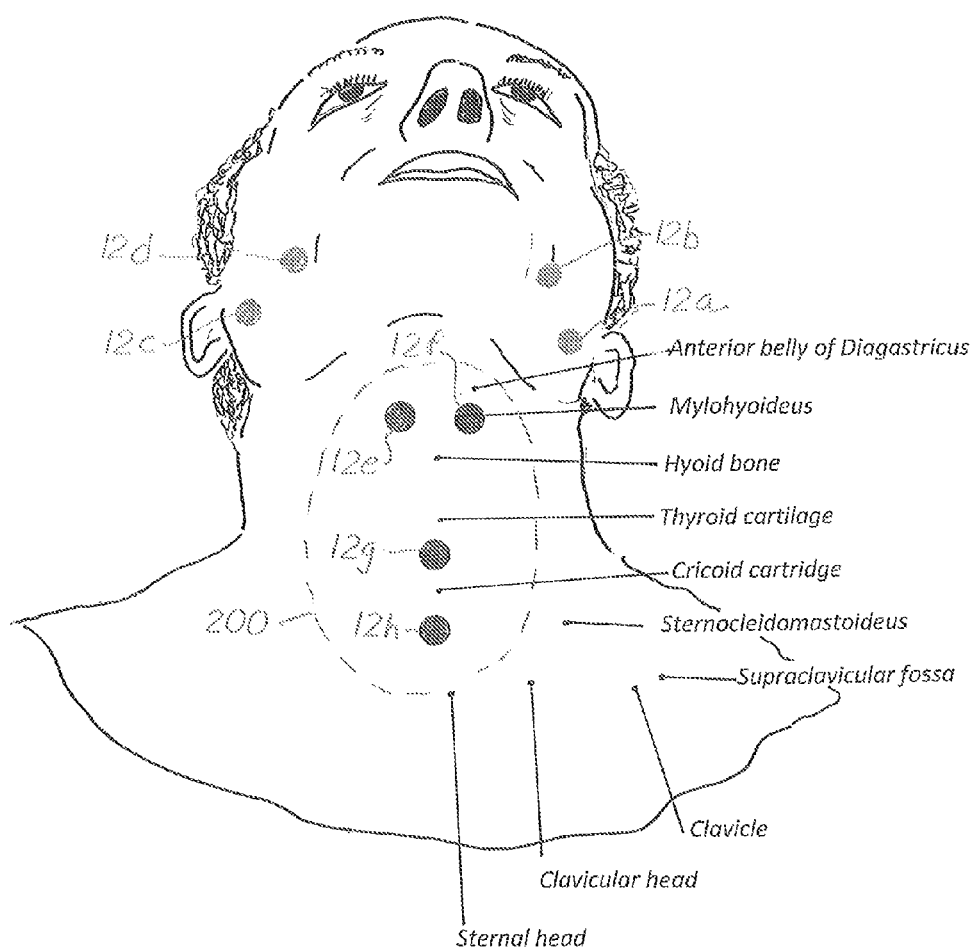
FIG. 9 is a front view of a patient showing the placement of four pharyngeal electrodes positioned on the skin of the pharyngeal region so that the top two electrodes are positioned on opposite sides of the midline of the pharyngeal region approximately at the mylohyodeus and the lower two electrodes are positioned longitudinally over the neck's longitudinal axis between the thyroid cartridge and the cricoid cartridge and between the cricoid cartridge and above the sterna head, respectively, and the two pairs of facial electrodes on opposite sides of the face.
Figure 10:
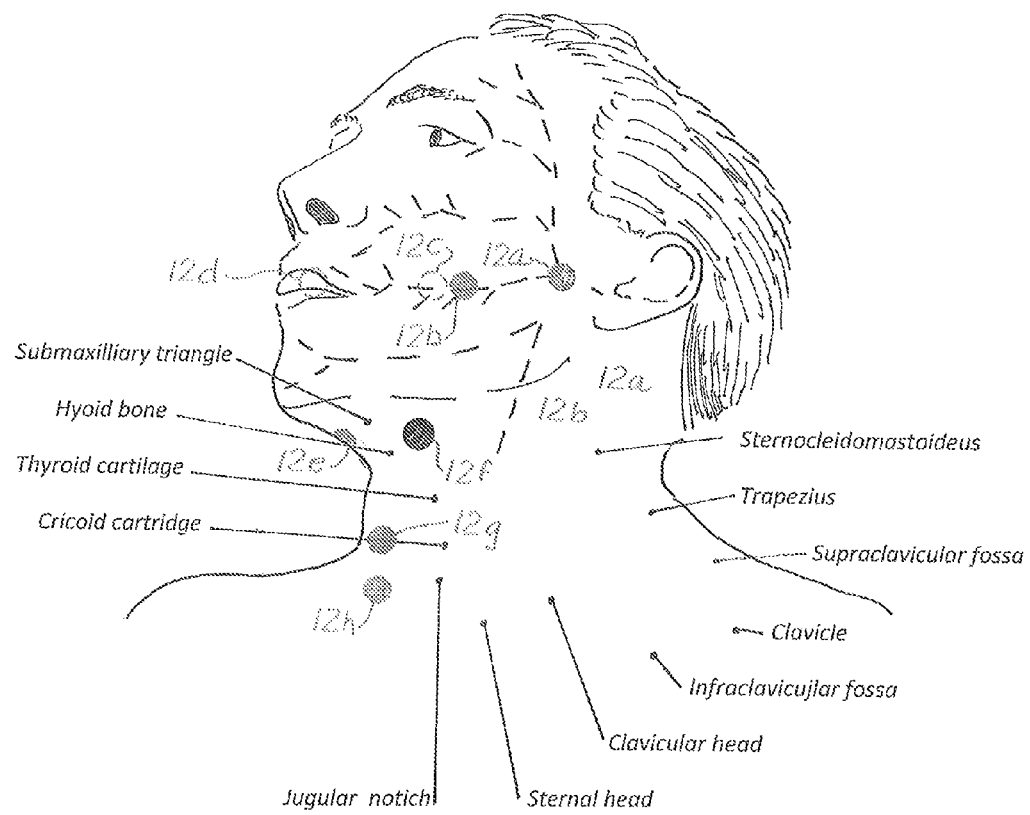
FIG. 10 is a front side perspective view of a patient presented in FIG. 9 more clearly showing the placement of the two electrodes on the side of the face.

In a fourth configuration, shown in FIG. 9, the four pharyngeal electrodes 12e-h are positioned on the skin of the pharyngeal region 200 so that the top two electrodes 12e, 12f are positioned on opposite sides of the midline of the pharyngeal region 200 approximately at the mylohyodeus and the lower two electrodes 12g, 12h being longitudinally aligned over the longitudinal axis between the thyroid cartridge and the cricoids cartridge and between the cricoid cartridge and above the sterna head, respectively.

Figure 5:
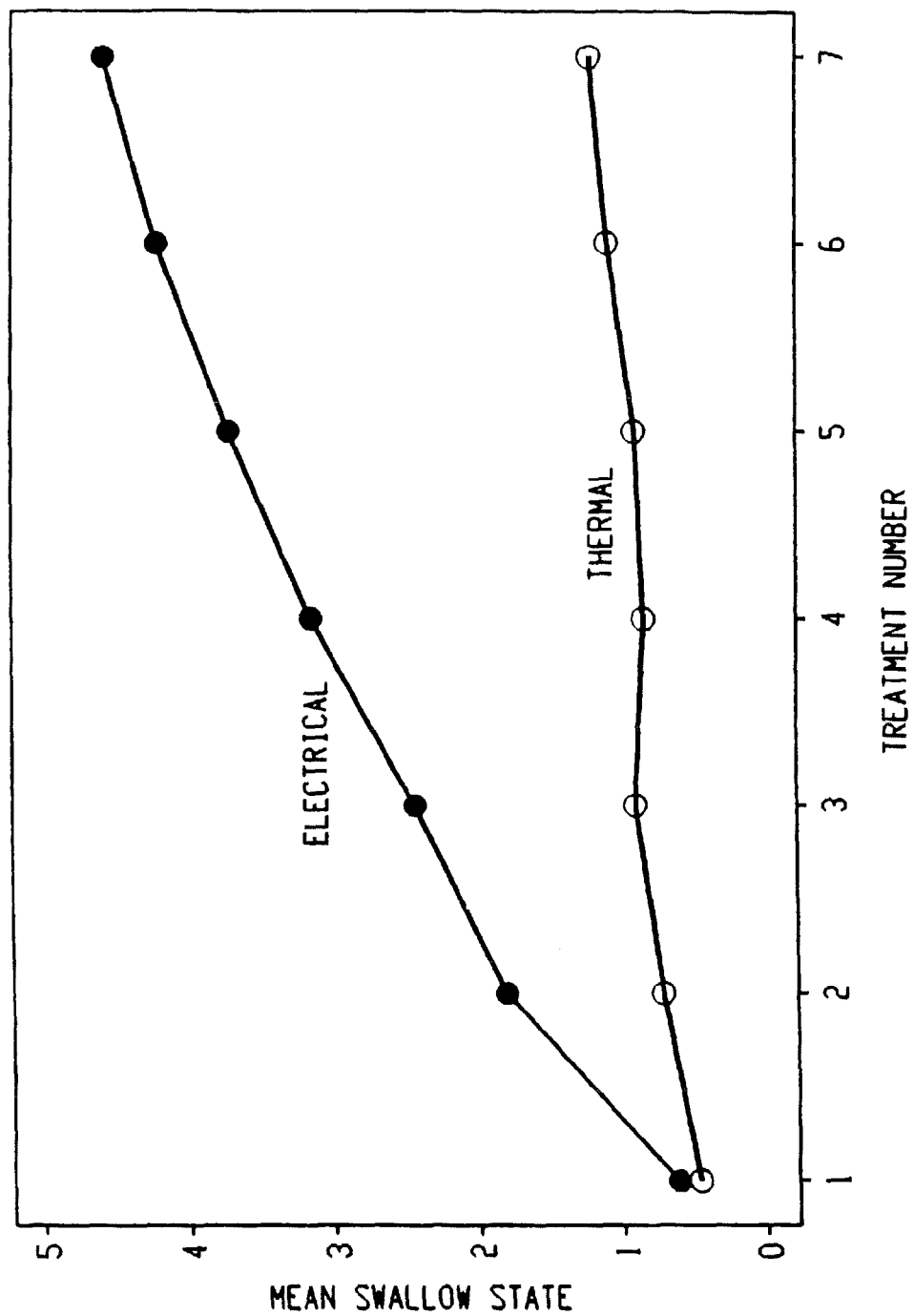
FIG. 5 is a graph showing the means swallow state over the treatment numbers.

The effectiveness of the electrical stimulation treatments and the thermal stimulation treatments is shown in FIG. 5. FIG. 5 is a graph illustrating the mean swallowing state achieved after electrical stimulation treatment sessions and thermal stimulation treatments.

The device and method for electrical pharyngeal and facial neuromuscular stimulation of the present invention provides an effective and non-invasive treatment for dysphagia that is faster and more effective than with pharyngeal neuromuscular stimulation alone.

While various embodiments of a method and device for artificially promoting a swallowing reflex have been disclosed, it should be understood that modifications and adaptions thereof will occur to persons skilled in the art. Other features and aspects of this invention will be appreciated by those skilled in the art upon reading and comprehending this disclosure. Such features, aspects, and expected variations and modifications of the reported results and examples are clearly within the scope of the invention where the invention is limited solely by the scope of the following claims.

In compliance with the statute, the invention described herein has been described in language more or less specific as to structural features. It should be understood, however, that the invention is not limited to the specific features shown, since the means and construction shown is comprised only of the preferred embodiments for putting the invention into effect. The invention is therefore claimed in any of its forms or modifications within the legitimate and valid scope of the amended claims, appropriately interpreted in accordance with the doctrine of equivalents.

I claim:

1. A device for treating dysphagia using electrical stimulation that simultaneously closes the mouth and activates a swallowing reflex in the pharyngeal region of the throat, comprising:
   a. a power source;
   b. eight electrode output plug connectors;
   c. a signal generator configured to provide four facial muscle output signals to four said electrode output plug connectors and configured to provide four pharyngeal region output signals to four said electrode output plug connectors simultaneously with said four facial muscle output signals, each said output signal having an intensity, a frequency, and a pulse duration;
   d. an output protector circuit for limiting said intensity of each said output signals;
   e. a treatment duration circuit for controlling the duration of operation of said signal generator;
   f. a ramp control circuit for controlling said intensity of each said output signal;
   g. a monitor for displaying operating parameters of said device;
   h. one electrode attached to each said electrode output plug connector;
   i. wherein said signal generator regulates said intensity, said frequency, and said pulse duration of said output signal in accordance with a procedure for closing the mouth prior to swallowing by applying said output signal to said output plug connectors connected to said electrodes attached to the facial region of a patient;
   j. wherein said signal generator regulates said intensity, said frequency, and said pulse duration of said output signal in accordance with a procedure for treating dysphagia by applying said output signal to said output plug connectors connected to said electrodes attached to the pharyngeal region of a patient;

k. wherein said treatment duration circuit and said ramp control circuit regulate said output signal in accordance with a procedure for treating dysphagia by applying said output signal to the pharyngeal region of the patient; and, i. wherein said output protector circuit is programmed to limit said intensity of said output signal in accordance with a treatment tolerance level of the patient.

2. A device according to claim 1, wherein said intensity of said of said output signal ranges from 0 to 4.4 milliamps.

3. A device according to claim 1, wherein said frequency of said output signal is approximately 80 Hertz.

4. A device according to claim 1, wherein said pulse duration is approximately 300 microseconds.

5. A device according to claim 1, wherein said output protector circuit limits said intensity of said output signal so as not to exceed approximately 4.4 milliamps.

6. A method for treating dysphagia by simultaneously stimulating muscles in the facial region that control closure of the mouth and by stimulating the pharyngeal region, comprising the following steps:

a. selecting an electrical stimulator with at least two pharyngeal stimulating electrodes and four facial stimulating electrodes, said electrical stimulator configured to simultaneously stimulate said pharyngeal and facial stimulating electrodes when properly positioned on a patient to cause swallowing;

b. attaching at least two said pharyngeal stimulating electrodes longitudinally over the anterior pharyngeal region of the throat that when stimulated initiate the swallowing reflex in the pharyngeal region;

c. attaching at least two pairs of facial stimulating electrodes to the facial regions on the face and around the mouth that when stimulated close the mouth, and, d. activating said electrical stimulator to simultaneously stimulate said pharyngeal and facial stimulating electrodes.

* * * * *